(12) United States Patent
Calderon et al.

(10) Patent No.: US 6,177,457 B1
(45) Date of Patent: Jan. 23, 2001

(54) PROCESS FOR THE PREPARATION OF INDACENE COMPOUND

(75) Inventors: Jose Maria Bueno Calderon, Getafe; Jesus Chicharro Gonzalo; Jose Fiandor Roman, both of Tres Cantos; Sophie Huss, Pozuelo, all of (ES); Brian Arthur Michael Rudd, St. Albans (GB)

(73) Assignee: Glaxo Wellcome S.A., Madrid (ES)

( * ) Notice: Under 35 U.S.C. 154(b), the term of this patent shall be extended for 0 days.

(21) Appl. No.: 09/180,440

(22) PCT Filed: May 6, 1997

(86) PCT No.: PCT/EP97/02285

§ 371 Date: Dec. 8, 1998

§ 102(e) Date: Dec. 8, 1998

(87) PCT Pub. No.: WO97/42195

PCT Pub. Date: Nov. 13, 1997

(30) Foreign Application Priority Data

May 8, 1996 (EP) .................................................. 96500058

(51) Int. Cl.⁷ ........................ A01N 43/16; C07D 319/14; C07D 315/00
(52) U.S. Cl. .......................... 514/456; 514/457; 514/460; 549/362; 549/416; 549/417
(58) Field of Search ...................... 549/362, 417, 549/416; 514/460, 456, 457

(56) References Cited

U.S. PATENT DOCUMENTS 5,854,280 * 12/1998 Gomez et al. ...................... 514/456
5,952,334 * 9/1999 Gomez et al. ...................... 514/261

OTHER PUBLICATIONS

Chemical Abstracts, vol. 107, No. 1, 1987 Columbus, Ohio, US; abstract No. 5745j, T. Ogita et al.: "Antibiotic zofimarin manufacture by Zofiela marina and its fungal activity" p. 540; XP002015901 & JP 06 240 292 A (SANKYO) Feb. 21, 1987.

* cited by examiner

*Primary Examiner*—John Kight
*Assistant Examiner*—Raymond Covington
(74) *Attorney, Agent, or Firm*—Nixon & Vanderhye

(57) ABSTRACT

A process for preparing compounds of the formula:

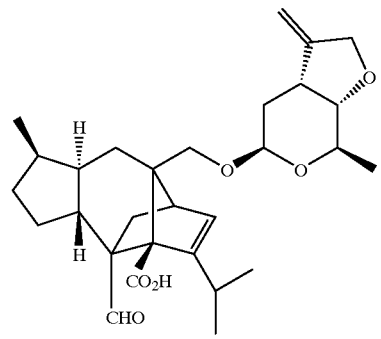

and intermediates for use in the process.

10 Claims, No Drawings

PROCESS FOR THE PREPARATION OF INDACENE COMPOUND

This application is a 35 U.S.C. §371 PCT/EP97/02285 filed May 6, 1997.

The present invention relates to a process for the preparation of an antifungal agent and to novel intermediates for use in the synthesis.

The compound of formula (I), pharmaceutically acceptable salts and metabolically labile esters thereof exhibit a particularly desirable spectrum of antifungal activity.

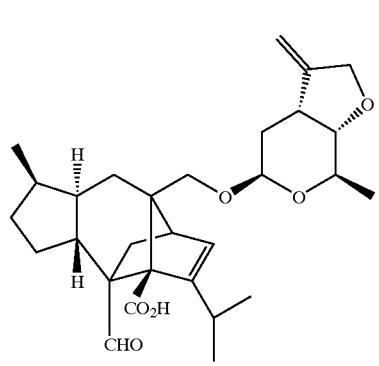

(I)

The present invention provides a process for the preparation of compound (I) which comprises cyclisation of a compound of formula (II) wherein L is a group capable of homolytic cleavage e.g. halogen such as bromine and R is hydrogen or a carboxyl protecting group,

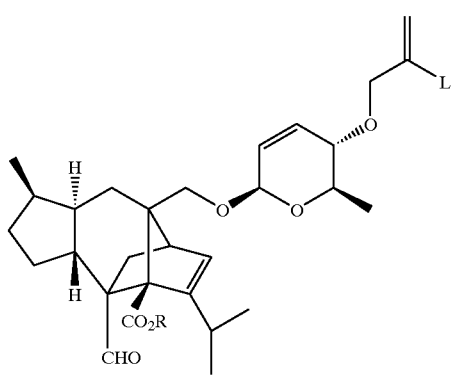

(II)

followed where desired or necessary by one or more of the following steps;

(i) removal of the carboxyl protecting group R;
(ii) isolation of the compound of formula (I) in the form of a a physiologically acceptable salt thereof;
(iii) conversion of the resultant compound of formula (I) into a metabolically labile ester thereof.

The cyclisation reaction is conveniently carried out using a radical chain carrier in the presence of a radical initiator. Suitable radical chain carriers for use in the reaction include tin radicals and a convenient source of such radicals are the trialkyltin hydrides for example tributyltin hydride. Suitable radical initiators include azoisobutyronitrile. Desirably the reaction is carried out in an aprotic solvent and with heating e.g. 80°–150°. Suitable aprotic solvents include hydrocarbons (e.g. octane) and aromatic hydrocarbons (e.g. toluene). Conveniently the cyclisation reaction is carried out using a compound of formula (II) wherein L is a bromine atom.

In a preferred embodiment of the invention the cyclisation reaction is carried out using a compound of formula (II) wherein R is a carboxyl protecting group. Suitable carboxyl protecting groups include acid or base labile ester groups such as substituted methyl esters e.g. pivaloyloxymethyl, or trimethylsilylethyloxymethyl.

The carboxyl protecting groups may be removed by conventional procedures well known to those skilled in the art. For example pivaloyloxymethyl may be cleaved by reaction with a suitable base such as an alkali metal alkoxide e.g. sodium methoxide in a suitable solvent such as an alcohol e.g. methanol.

The trimethylsilylethyloxymethyl ester may be cleaved by reaction with fluoride ions e.g. tetrabutylammonium fluoride in a suitable aprotic solvent such as an ether e.g. tetrahydrofuran.

Suitable pharmaceutically acceptable salts of the compounds of formula (I) include inorganic base salts such as alkali metal salts (for example sodium and potassium salts) and ammonium salts and organic base salts. Suitable organic base salts include amine salts such as trialkylamine (e.g. triethylamine), dialkylamine (e.g. dicyclohexylamine), optionally substituted benzylamine (e.g. phenylbenzylamine or p-bromobenzylamine), procaine, ethanolamine, diethanolamine, N-methylglucosamine and tri (hydroxymethyl)methylamine salts and amino acid salts (e.g. lysine and arginine salts).

Salts of compounds of formula (I) may be conveniently formed by treating a compound of formula (I) with an appropriate salt or base. Thus, for example, salts may conveniently be prepared by treating a compound of formula (I) with a salt or a base selected from sodium or potassium hydroxide, hydrogen carbonate, carbonate or acetate (e.g. potassium hydroxide, potassium hydrogen carbonate, sodium hydrogen carbonate or potassium acetate), ammonium acetate, calcium acetate or an organic amine e.g. L-lysine as appropriate. The salt may, for example, be prepared by adding the appropriate salt or base (if necessary as an aqueous solution) to a solution or suspension of the compound of formula (I) in a suitable solvent such as an alcohol (e.g. methanol) or dioxane at temperatures of for example 0° C. to 80° C. and conveniently at about room temperature.

Pharmaceutically acceptable salts may also be prepared from other salts including other pharmaceutically acceptable salts of the compounds of formula (I), using conventional methods.

The compound of formula (II) may be prepared by alkylation of the corresponding alcohol (III);

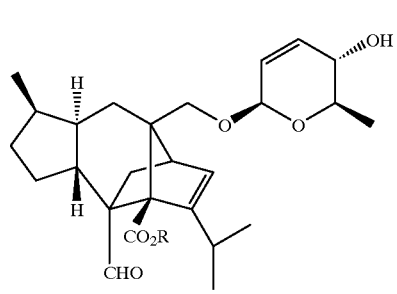

(III)

by reaction with the compound (IV);

$$L^1CH_2C(L)=CH_2 \quad (IV)$$

wherein $L^1$ is a leaving group such as a halogen e.g. bromine or iodine or an ester e.g. mesylate or tosylate and L has the meanings defined above.

The reaction is carried out in the presence of a base such as aqueous sodium hydroxide and conveniently in a water immiscible organic solvent such as dichloromethane and in the presence of a phase transfer catalyst e.g. cetyltrimethylammonium bromide.

For this reaction it is desirable that any carboxyl protecting group is not a base labile protecting group. A particularly suitable carboxyl protecting group for use in the reaction is the trimethylsilylethyloxymethyl ester.

In an alternative process the compound of formula (II) may be prepared by carrying out an elimination reaction on the diol ( V) or the stereoisomer (VI) thereof;

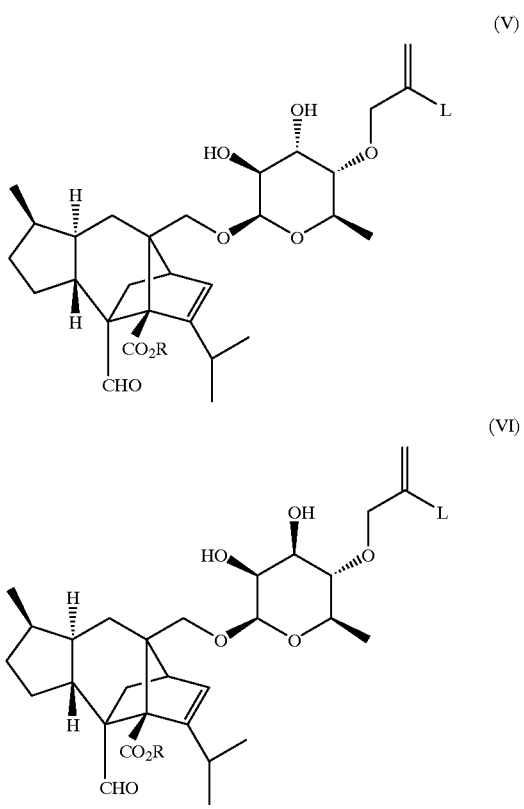

wherein L and R have the meanings defined above.

Thus in one embodiment of the process the diol (V) may be converted into compound (II) by reaction with phenyl chlorothionoformate in the presence of a base e.g. a tertiary organic base such as triethylamine and 4-dimethylaminopyridine and then treating the resultant di-phenoxythiocarbonate with a source of hydride radicals such as a trialkyltin hydride e.g. tributyltin hydride.

The reaction with phenyl chlorothionoformate is conveniently carried out in an aprotic solvent such as a halohydrocarbon e.g. dichloromethane. The reaction of the resultant dithionocarbonate with the trialkyltin hydride is conveniently carried out in an aromatic hydrocarbon such as toluene and with heating e.g. at reflux.

It will be appreciated if the reaction with the trialkyltin hydride is carried out in the presence of a radical initiator such as azoisobutyronitrile then the compound of formula (II) thus formed will be converted directly into a compound of formula (I). Thus the invention also provides a process for the preparation of a compound of formula (I) which comprises reacting the dithionocarbonate derivative of the diol (V) with a trialkyltin hydride in the presence of a radical initiator; followed where necessary or desired by removal of the carboxyl protecting group.

The diol (VI) may be converted into the required compound (II) by reaction with phenyl chlorothionoformate in the presence of dibutyltin oxide and in a solvent such as toluene, or by reaction with thiocarbonyl diimidazole and treatment of the resulting cyclic thionocarbonate with a trialkylphosphite for example trimethylphosphite.

Alternatively the diol (Vl) may be treated with iodine or triiodoimidazole or iodoform and imidazole in the presence of triphenylphosphine. The reaction is conveniently carried out in an aprotic solvent such as a hydrocarbon e.g. toluene and with heating e.g. at reflux.

The diol (V) may be prepared by alkylation of the triol (VII) wherein R is as defined in formula (II) by reaction with a compound of formula (IV).

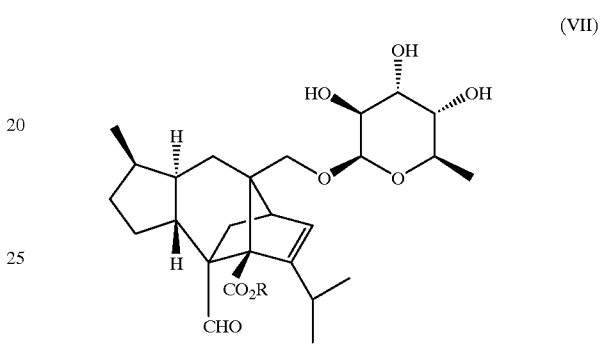

The reaction is carried out in the presence of dibutyltin oxide or dibutyltin dimethoxide and in a solvent such as toluene. Conveniently the reaction is also carried out in the presence of fluoride ions.

The triol of formula (VII) wherein R is a carboxyl protecting group may be prepared by esterifying the corresponding compound of formula (VII) wherein R is hydrogen using conventional procedures for preparing such protected carboxylic acid derivatives. Thus compounds wherein R is a substituted methyl group may be prepared by reaction with the corresponding substituted methyl halide e.g. chloride, or bromide in the presence of a base such as a tertiary organic amine such as trialkylamine, or an alkali metal hydroxide, carbonate or bicarbonate.

The diol of formula (VI) may be prepared by reaction of compound (VIII) wherein R is as defined in formula (II)

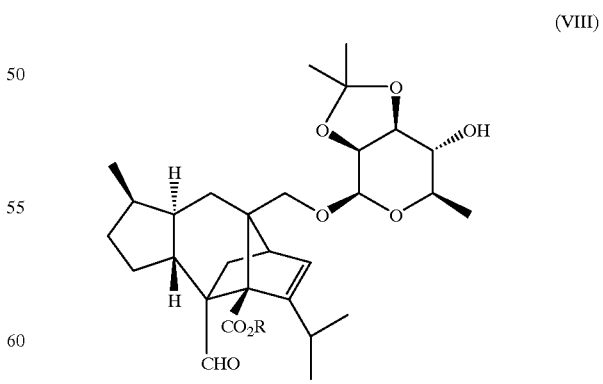

with the compound (IV) using the alkylation conditions described above for the preparation of compound (II) from compound (III) followed by treatment with hydrochloric acid to remove the acetonide protecting group.

The compound of formula (III) may be prepared by reaction of the triol (IX) with p-toluenesulphonic acid and 2,2-dimethoxypropane in acetone as solvent.

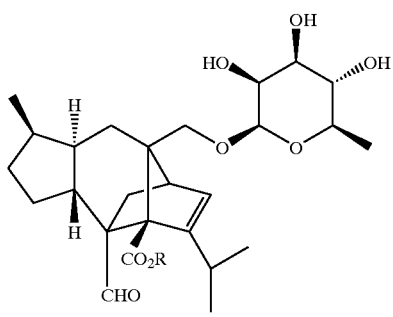

(IX)

The triol (IX) wherein R is a carboxyl protecting group may be prepared from the corresponding compound (IX) wherein R is hydrogen using conventional procedures. For example using the conditions described above for converting the triol (VII) wherein R is hydrogen into the corresponding compound wherein R is a carboxyl protecting group.

The alcohol (III) may be prepared from the triol (VIII) or (IX).

Reaction of the trio (VII) with 2,2-dimethoxypropane and p-toluenesulphonic acid in acetone as solvent yields the acetonide (X).

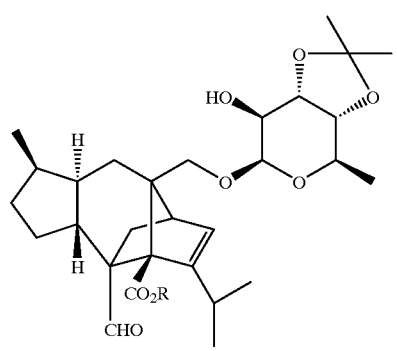

(X)

The acetonide (X) may then be converted into the iododiol (XI).

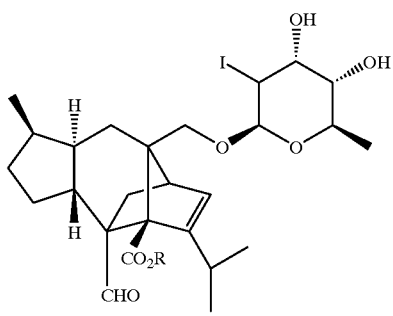

(XI)

by reaction with iodine or triodoimidazole or iodoform and imidazole in the presence of triphenylphosphine, followed by removal of the acetonide protecting group.

The iododiol (XI) may be converted into the required alcohol (III) by reaction with iodine, imidazole, triphenylphosphine and zinc in a suitable solvent e.g. toluene and with heating.

The alcohol (III) may also be prepared by reaction of compound (XII)

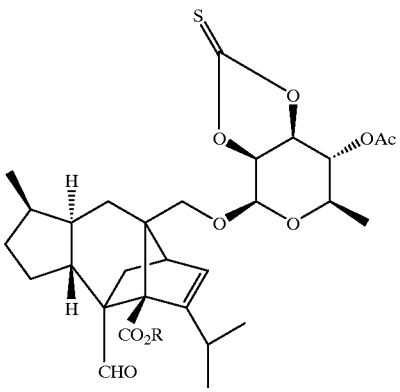

(XII)

with a trialkylphosphite such as trimethylphosphite followed by treatment with suitable base e.g. sodium hydroxide or sodium methoxide to remove the O-acetyl protecting group.

The compound of formula (XII) may be prepared by reaction of the triol (IX) with dibutyltin oxide or dibutyltin dimethoxide and phenyl chlorothionoformate in a solvent such as toluene and then treatment of the resulting product with acetyl chloride in the presence of a suitable organic base such as 4-dimethylaminopyridine.

In the synthesis of compound (I) from either the triol (VII) or (IX) it may be desirable to change the nature of the carboxyl protecting group R at a particular step in the synthesis and such changes are within the scope of the present invention.

The triol of formula (VII) wherein R is a hydrogen atom may be prepared by the procedures described in WO96/14326.

The intermediate compounds of formulae (III), (V), (VI). (VIII), (X), (XI) and (XII) are novel compounds and represent further aspects of the invention.

The compounds of formula (IV) are either known compounds or may be prepared by analogous methods to those used to prepare the known compounds.

The triols of formula (IX) are novel compounds and represent a further feature of the invention.

The triol of formula (IX) wherein R is hydrogen may conveniently be prepared according to the fermentation process described hereinafter.

The fermentation process comprises cultivating a microorganism capable of producing the compound of formula (IX; R=H) and thereafter isolating the compound of formula (IX; R=H) or a salt thereof e.g. a lithium salt from the culture in substantially pure form.

Microorganisms capable of producing the compound of formula (IX; R=H) will conveniently be mutant strains of *Sordaria araneosa* which can readily be identified by screening survivors of mutagenesis by analysing a test sample obtained from fermentation of the microorganism using standard methodology. In particular, the microorganism to be conveniently used is a mutant strain of *Sordaria araneosa* deposited in the permanent culture collection of the CAB International Mycological Institute, Genetic Resource Reference Collection, Bakeham Lane, Egham, Surrey TW20 9TY, England. The strain was received by the Institute on Dec. 8, 1995 and was subsequently given the accession number IMI 369677 and confirmation of viability on Dec. 15, 1995. The Institute is an International Depository authority recognised under the Budapest Treaty.

The microorganism IMI369677 was isolated following N-methyl-N'-nitro-N-nitrosoguanidine (MNNG) mutagenesis of ascospores of IMI362184, which is itself a mutant of NRRL3196, derived by MNNG mutagenesis. The characteristics of IMI369677 are essentially similar to those described in British Patent specification No. 1,162,027 for NRRL3196, except that IMI369677 produces Compound (IX, R=H) as a major product under the same conditions used for sordarin production by NRRL3196.

The present invention provides in a further aspect the microorganism IMI 369677 per se and mutants thereof.

The following examples hereinafter illustrate aspects of the present invention and are not intended to limit the invention in any way.

INTERMEDIATE 1

[1R-(1α,3aβ,4β,4aβ,7β,7aα,8aβ)]8a[6-Deoxy-2,3-O-thionocarbonyl-β-D-mannopyranosyloxymethyl]-4-formyl-4,4a,5,6,7,7a,8,8a-octahydro-7-methyl-3-(1-methylethyl)-1,4-methano-s-indacene-3a(1H) carboxylic acid, trimethylsilylethyloxymethyl ester.

To a cooled solution of Example 1 (325 mg) in dry tetrahydrofuran (3 ml) were added at 0° C. neat triethylamine (0.135 ml) and trimethylsilylethyloxymethyl chloride (0.132 ml ) under a nitrogen atmosphere. The mixture was stirred at 0° C. until completion of the reaction (2 hours.) Sodium hydrogen carbonate solution added with vigorous stirring for 30 minutes and then water (10 ml) was added. The suspension was extracted with ethyl acetate (15 ml). The organic layer was washed with brine (10 ml) and dried over magnesium sulfate. Evaporation of the solvent gave a syrup which was used in the next step without further purification.

A suspension of the product before mentioned, dibutyltin oxide (320 mg) and molecular sieves (300 mg) in dry toluene (12 ml) was heated at reflux for 2 hours and then cooled to room temperature under $N_2$ atmosphere. A solution of phenyl chlorothionoformate (177 µl) in toluene (3 ml) was added dropwise and the mixture stirred at room temperature until completion of the reaction (approx. 4 hours). The mixture was poured onto a short column of silica gel (Ø=2 cm, 5 cm) containing a bed of celite (1 cm) at the top and it was eluted with toluene (50 ml) and air dried. The product was obtained by elution with hexane:ethyl acetate v:v 10:1 and 4:1. The title compound (400 mg) was obtained as a white foam.

δ ($^1$H, CDCl$_3$): 9.53 (s, 1H, CHO), 6.13 (dd, 1H, H2, J=1.5 and 3.6 Hz), 5.46 and 5.24 (2d, 2H, OCH$_2$O, J=5.7 Hz), 4.92–4.82 (m, 2H, H2'+H3'), 4.75 (d, 1H, H1', J=3 Hz), 4.21 (m, 1H, H4'), 3.98 (d, 1H, 8aCH$_2$(1H), J=9 Hz); 3.8–3.5 (m, 4H, 8aCH$_2$(1H)+OC$\underline{H}_2$CH$_2$Si+H5'), 2.85 (t, 1H, H1, J=4.2 Hz), 2.54 (d, 1H, OH, J=5.1 Hz), 2.29 (m, 1H, CH(CH$_3$)$_2$).

INTERMEDIATE 2

[1R-(1α,3aβ,4β,4aβ,7β,7aα,8aβ)] 8a[4-O-Acetyl-6-deoxy-2,3-O-thionocarbonyl-β-D-mannopyranosy-loxymethyl]-4-formyl-4,4a,5,6,7,7a,8,8a-octahydro-7-methy-3-(1-methylethyl)-1,4-methano-s-indacene-3a(1H) carboxyiic acid, trimethylsilylethyloxymethyl ester.

To a solution of 4-dimethylaminopyridine (733.2 mg) in dry tetrahydrofuran (10 ml) was added dropwise at 0° C. under nitrogen atmosphere neat acetyl chloride (355 µl) and the mixture stirred until complete precipitation of the white solid was achieved. Intermediate 1 (1.2 g) in dry THF (3 ml) was then added and the mixture stirred at room temperature until completion (approx 1 hour). Methanol (1 ml) was added and the mixture concentrated to dryness to give a solid which was partitioned between ethyl acetate (100 ml) and 1N hydrochloric acid (100 ml). The organic layer was washed with 1N hydrochloric acid and brine (100 ml), dried over MgSO$_4$ and concentrated on silica to give a powder which was placed at the top of a silica gel column. The product was purified by eluting with mixtures of ethyl acetate:hexane v:v 1:10, 1:9, 1:6 and 1:5. Evaporation of the solvent gave the title compound (1.1 g,) as a white foam when dried under vacuum.

δ ($^1$H, CDCl$_3$): 9.64 (s, 1H, CHO), 6.13 (dd, 1H, H2, J=1.2 and 3.3 Hz), 5.64 (dd, 1H, H4', J=6 and 10.2 Hz), 5.46 and 5.23 (2d, dH, OCH$_2$O, J=6.3 Hz), 4.98–4.86 (m, 2H, H2'+H3'), 4.80 (d, 1H, H1', J=3 Hz), 4.02 (d, 1H, 8aCH$_2$ (1H), J=9 Hz), 3.79–3.59 (m, 4H, 8aCH$_2$(1H)+OC$\underline{H}_2$CH$_2$Si+H5'), 2.86 (t, 1H, H1, J=3.9 Hz), 2.29 (m, 1H, CH(CH$_3$)$_2$), 2.12 (s, 3H, CH$_3$CO).

INTERMEDIATE 3

[1R-(1α,3aβ,4β,4aβ,7β,7aα,8aβ)]8a[4-O-Acetyl-2,3-didehydro-2,3,6-trideoxy-β-D-allopyranosyloxy methyl]-4-formyl-4,4a,5,6,7,7a,8,8a-octahydro-7-methyl-3-(1-methylethyl)-1,4-methano-s-indacene-3a(1H) carboxylic acid, trimethylsilylethyloxymethyl ester.

A solution of Intermediate 2 (675 mg) in trimethylphosphite (125 ml) was kept at reflux under nitrogen atmosphere for 9 hours. The solution was cooled to room temperature and then poured onto a mixture of water (125 ml) and ethyl acetate (125 ml). The two phases were stirred for two hours and the organic phase washed with brine (2×100 ml) and dried over MgSO4. Concentration to dryness and purification by flash chromatography (hexane:ethyl acetate v:v 7:1) afforded the title compound (259 mg) as a syrup.

δ ($^1$H, CDCl$_3$): 9.69 (s, 1H, CHO), 6.07 (dd, 1H, H2, J=1.5 and 3.6 Hz), 5.91–5.81 (m, 2H, H2'+H3'), 5.44 and 5.27 (2d, 2H, OCH$_2$O, J=6.3 Hz), 5.02 (m, 1H, H4'), 4.96 (m, 1H, H1'), 3.92 (d, 1H, 8aCH$_2$(1H), J=9.3 Hz), 3.85–3.66 (m, 4H, 8aCH$_2$(1H)+OC$\underline{H}_2$CH$_2$Si+H5'), 2.78 (t, 1H, H1, J=3.9 Hz), 2.28 (m, 1H, CH(CH$_3$)$_2$), 2.06 (s, 3H, CH$_3$CO).

INTERMEDIATE 4

[1R-(1α,3aβ,4β,4aβ,7β,7aα,8aβ]8a[6-deoxy-β-D-mannopyranosyloxy)methyl]4-formyl-4,4a,5,6,7,7a,8,8a-octahydro-7-methyl-3-(1-methylethyl)-1,4-methano-s-indacene-3a(1H) carboxylic acid, diphenylmethyl ester.

To a solution of Example 1 (5 g) in a mixture of CH$_2$Cl$_2$/MeOH v/v 95/5, diphenyidiazomethane (0.031 mol) was added carefully. The reaction mixture was stirred at room temperature until no starting material was detected by TLC. 1N HCl (120 ml) was added with vigorous stirring until the colour of the mixture became yellow. The organic phase was concentrated at reduced pressure and redissolyed in ethyl acetate, washed with saturated NaHCO$_3$, dried over Na$_2$SO$_4$ and concentrated to dryness. The crude thus obtained was purified by flash chromatography on silica gel (CH$_2$Cl$_2$/MeOH v/v 23:1) to afford 5.1 g of the title compound as a white foam when dried under vacuum.

δ ($^1$H, CDCl$_3$): 9.74 (s,1H,CHO); 7.45–7.25 (m,10H, Ph$_2$); 6.99 (s,1H,C$\underline{H}$Ph$_2$); 6.05 (dd, 1H, H2, J=1.5 and 3.3 Hz); 4.23 (d, 1H, H1', J=0.6 Hz); 4.09 and 3.77 (2d, 2H, 8aCH$_2$, J=9.3 Hz); 3.95 (m, 1H, H2'); 3.5–3.35 (m, 2H, H3'+H4'); 3.24 (dq, 1H ,H5', J=6.3 and 9Hz), 2.75 (t, 1H, H1, J=3.6 Hz).

INTERMEDIATE 5

[1R-(1α,3aβ,4β,4aβ,7β,7aα,8aβ)][8a[6-deoxy-4-O-(2-bromo-2-propenyl)-β-D-mannopyrano-syloxy)methyl]-4- formyl-4,4a,5,6,7,7a,8,8a-octahydro-7-methyl-3-(1-methylethyl)-1,4-methano-s-indacene-3a(1H) carboxylic acid, pivaloyloxymethyl ester.

The Intermediate 4 (5.1 g) was dissolved in dry acetone (95 ml) and to this solution were added 2,2-dimethoxypropane (3.94 ml) and p-toluene sulphonic acid (76 mg). The mixture was stirred at room temperature under nitrogen until completion of the reaction (30 min approx.). Solid NaHCO$_3$ (1.5 g) was added carefully and the solvent was concentrated at reduced pressure. The crude was redissolved in ethyl acetate and washed with brine. The organic phase was separated, dried over Na$_2$SO$_4$ and concentrated to give a white foam.

To a solution of the white foam (1 g) and cetyltrimethylammonium bromide (53.1 mg) in dry dichloromethane (6 ml) was added sodium hydroxide (50% in water, 5 ml) and the mixture stirred vigorously for 10 min. 2,3-dibromo-1-propene (95%, 476 µl) was added and the mixture stirred at room temperature. Two additional portions of 2,3-dibromo-1-propene (2×100 µl) and cetyltrmethyl ammonium bromide (2×15 mg) were added over a period of 3.5 h. Once the reaction was concluded (TLC control showed disappearance of starting material after 4 h) the two phases were diluted with dichoromethane (50ml) and water(50 ml) and the organic layer was washed with 1N HCl (100 ml), saturated NaHCO$_3$ (100 ml) and brine (2×100 ml), then it was dried over MgSO$_4$ and concentrated to dryness.

The syrup thus obtained was dissolyed in dry dichloromethane (10 ml) and treated with TFA (300 µl) at 0° C. until disapearance of the starting material. The solution was diluted with dichloromethane (50 ml), washed with 10% NaHCO$_3$ and brine (100 ml), dried over MgSO$_4$ and concentrated to give a syrup which was dissolved in 15 ml of a mixture of THF/MeOH (v/v 2:1). To this solution was added dropwise 1N HCl (5 ml) over a period of 10 min and the mixture heated to 50° C. (approx. 70° C. oil bath) until completion of the reaction. The mixture was carefully neutralized with solid NaHCO$_3$ and the solvent removed to dryness. The residue was partitioned between ethyl acetate and water and the organic layer washed twice with brine (2×100 ml) and dried over MgSO$_4$. Evaporation of the solvent gave 928 mg of a residue which was dissolved in dry DMF (14 ml). Water (1.4 ml) and NaHCO$_3$ (1 g) were added and the mixture stirred at room temperature for 30 min. The mixture was heated to 30–35° C. (oil bath) and three portions of pivaloyloxymethyl chloride (3×150 µl) were added over a period of 1 h. Once the reaction was concluded (approx. 3.5 h) the mixture was poured onto ethyl acetate (50 ml) and it was quenched by adding carefully 1N HCl (50 ml). The two phases were partitioned and the organic one washed with 1N HCl (5×50 ml), water (50 ml) and brine (50 ml). Then it was dried over Na$_2$SO$_4$ and purified by flash chromatography (silica gel, CH$_2$Cl$_2$ and MeOH/CH$_2$Cl$_2$ v/v 1:100) to afford 700 mg of pure product as a white foam when dried under vacuum.

δ ($^1$H, CDCl$_3$): 9.70 (s,1H,CHO); 6.06 (dd, 1H, H2, J=1.5 and 3.6 Hz); 5.92 (dd, 1H, CH$_2$=, J=0.9 and 2.7 Hz); 5.90 and 5.78 (2d, 2H, OCH$_2$O, J=5.4Hz); 5.60 (d, 1H, CH$_2$=, J=1.5 Hz); 4.46 and 4.32 (2d, 2H, CH$_2$O, J=13.2 Hz); 4.28 (d, 1H, H1', J=0.9 Hz); 3.95 and 3.89 (m, 2H, H2'+8aCH$_2$ (1H)); 3.71 (d, 1H, 8aCH$_2$(1H), J=9 Hz); 3.61 (m, 1H, H3'); 3.3–3.2 (m,2H, H4'+H5'); 2.75 (t, 1H, H1, J=3.9 Hz); 2.64 (d,1H, OH, J=8.1 Hz); 2.32–2.2 (m, 2H, OH+CH(CH$_3$)$_2$).

INTERMEDIATE 6

[1R-(1α,3aβ,4β,4aβ,7β,7aα,8aβ)]8a[[1S,7R,9R]-2,8-dioxa-9-methyl-4-methylene-cis-bicyclo[3,4,0]-non-7-yl-oxymethyl]-4-formyl-4,4a,5,6,7,7a,8,8a-octahydro-7-methyl-3-(1-methylethyl)-1,4-methano-s-indacene-3a(1H) carboxylic acid, pivaloyloxymethyl ester.

Method A

A solution of Example 3 (600 mg), tributyltin hydride (375 µl) and azoisobutyronitrile (7.2 mg) in dry toluene (20 ml) was degassed with an Argon stream for 15 min. and then heated to 83° C. (approx. 95° C. oil bath) until no starting material was detected by TLC (approx. 45 min). The solution was cooled to room temperature and carbon tetrachloride (1 ml) was added. After 1 h solid iodine was carefully added until an orange colour appeared and the mixture stirred for 30 min. Water (10 ml), solid sodium metabisulfite (500 mg) and solid potassium fluoride (200 mg) were added and the mixture vigorously stirred overnight.

The white solid was removed by filtration and all the solvents evaporated to dryness. Diethyl ether (3×50 ml) was added and the mixture stirred for 1 h. Filtration and evaporation of the solvent gave a residue which was purified by flash chromatography (silica gel, hexane/ethyl acetate v/v 30:1, 25:1, 20:1 and 18:1) to afford 360 mg of the desired compound as an oil (70% yield).

Method B

A solution of Intermediate 17 (270 mg) in dry toluene (12 ml) was degassed with an argon stream at room temperature for 1 hour. Tributyltin hydride (110 µl) was added and the reaction mixture was heated to reflux. More tributyltin hydride (110 µl) and azoisobutyronitrile (5 mg) were added after 5 minutes and the reflux was maintained for a further 40 minutes. After cooling, carbon tetrachloride (1 ml) was added and the solution stirred at room temperature for 1 hour. A dilute solution of iodine in diethyl ether was then added until a faint coloration persisted. The solvent was then removed in vacuo and the residue taken up in diethyl ether and washed several times with a saturated aqueous solution of potassium fluoride until no more precipitation o tributyltin fluoride was observed. The organic layer was dried and evaporated to give a residue which was flash chromatographed on silica gel eluting with hexane:acetone (96:4) to afford the title compound (80 mg).

INTERMEDIATE 7

[1R-(1α,3aβ,4β,4aβ,7β,7aα,8aβ)]8a-[6-Deoxy-2,3-O-isopropyliden-β-D-mannopyranosyloxy methyl]-4-formyl-4,4a,5,6,7,7a,8,8a-octahydro-7-methyl-3-(1-methylethyl)-1,4-methano-s-indacene-3a(1H)-carboxylic acid, trimethylsilylethyloxymethyl ester.

To a solution of Example 1 (2 g) in dry tetrafrdrofuran (20 ml) were added at 0° C. under nitrogen atmosphere tnithylamine (0.87 ml) and trimethylsilylethyloxymethyl chloride in dry tetrahydrofuran (5 ml). After 1 hour methanol (1 ml) was added and the mixture strred for 30 minutes. Evaporation of the solvent gave a residue which was partoned between ethyl acetate and water (400 ml v:v 1:1). The organic layer was washed with water (200 ml) and brine (2×200 ml) then dried over sodium sulfale. Concentration to dryness gave a crude product which was dissolved in dri acetone (40 ml) and treated successively with p-toluenesulphonic acid (40 mng) and 2,2-dimethoxypropane (2 ml). After stirring for 45 minutes anhydrous potassium carbonate (4 g) was added. the mixture stirred for 30 minutes and then filtered and the filtrate concentrate to dryness. The syrup thus obtained was partitioned between water and ethyl acetate (400 ml v:v 1:1). The organic layer was washed with brine (200 ml) and dried over sodium sulfate. Evaporation of the solvent at reduced pressure gave a crude product which was purified by flash chromatography (eluent hexane and hexane:acetone v:v 9:1) to yield the title compound (1.74 g).

δ ($^1$H, CDCl$_3$): 9.70 (s, 1H, CHO), 6.07 (dd, 1H, H2, J=1.2 and 3.6 Hz), 5.44 and 5.25 (2d, 2H, OCH$_2$O, J=6.3 Hz), 4.57 (d, 1H, H1', J=2.4 Hz), 4.19 (dd, 1H, H2', J=2.4 and 6.3 Hz), 4.20 (m, 2H, 8aCH$_2$(1H)+H3'), 3.8–3.6 (m, 4H, OC$\underline{H}_2$CH$_2$Si+8aCH$_2$(1H)+H4'), 3.33 (dq, 1H, H5', J=6.3 and 9.9 Hz), 2.85 (t, 1H, H1, J=3.9 Hz), 2.29 (m, 1H, CH(CH$_3$)$_2$), 2.14 (d, 1H, OH, J=3.9 Hz).

INTERMEDIATE 8

[1R-(1α,3aβ,4β, 4aβ,7β,7aα,8aβ)]8a-[4-O-(2-Bromo-2-propenyl)-6-dexoy-2,3-O-isopropylidene-β-D-mannopyranosyloxymethygl]-4-formyl4,4a,5,6,7,7a,8,8a-octahydro-7-methyl-3-(1-methylethyl)-1,4-methano-s-indacene-3a(1H)-carboxylic acid, trimethylsilylethyloxymethyl ester.

To a solution of Intermediate 7 (1.06 g) in dry dichloromethane (5 ml) was added 50% sodium hydroxide in water (5 ml) and cetyltrimethylammonium bromide (58 mg). The mixture was vigorously stirred for 1 minute and 2,3-dibromo-1-propene was then added at room temperature. After 4 hours the reaction was poured onto brine (10 ml) and partitioned. The organic phase was washed with 1N hydrochloric acid (50 ml) and brine (2×100 ml), then dried over magnesium sulfate and concentrated to dryness to give a crude product which was purified by flash chromatography on silica gel (eluent hexane:ethyl acetate v:v 20:1 and 15:1) to afford the title compound (920 mg) as an oil.

δ ($^1$H, CDCl$_3$): 9.70 (s, 1H, CHO), 6.07 (dd, 1H, H2, J=1.5 and 3.6 Hz), 5.92 and 5.61 (2m, 2H, H$_2$C=), 5.44 and 5.26 (2d, 2H, OCH$_2$O, J=6.3 Hz), 4.55 (d, 1H, H1', J=2.1 Hz), 4.38 and 4.31 (2d, OCH$_2$C=, J=13.8 Hz), 4.1 (m, 2H, H2'+H3'), 4.00 (d, 1H, 8aCH$_2$(1H), J=9.3 Hz), 3.8–3.65 (m, 3H, OC$\underline{H}_2$CH$_2$Si+8aCH$_2$(1H)), 3.51–3.36 (m, 2H, H4'+H5'), 2.84 (t, 1H, H1, J=3.9 Hz), 2.28 (m, 1H, CH(CH$_3$)$_2$).

INTERMEDIATE 9

[1R-(1α,3aβ,4β,4aβ,7β,7aα,8aβ)]8a-[4-O-(2-bromo-2-propenyl)-2,3,0-thionocarbonyl-β-D-mannopyranosyloxymethyl]-4formyl-4,4a,5,6,7,7a,8,8a-octahydro-7-methyl-3-(1-methylethyl)-1,4-methano-s-indacene-3a(1H)-carboxylic acid, pivaloyloxymethyl ester.

To a solution of Intermediate 8 (790 mg) in methanol (15 ml) was added water until the mixture become cloudy. Then p-toluensulphonic acid (155 mg) was added and the mixture stirred at room temperature for 24 hours. The methanol was evaporated at reduced pressure and the resulting suspension extracted with ethyl acetate. The solvent was removed under reduced pressure, the residue dissolyed in dry toluene and to this solution were added triethylamine (0.74 ml) and pivaloyloxymethyl chloride (0.39 ml). This solution was heated to reflux. After 2 hours another portion of triethylamine (1.48 ml) and pivaloyloxymethyl chloride (0.78 ml) were added and the reaction stirred at room temperature overnight. Thiocarbonyldiimidazole (477 mg) was then added and the resulting solution heated to reflux until completion and then cooled to room temperature. Silica gel (500 mg) was added and the solvent evaporated. After chromatography (hexane:ethyl acetate v:v 1:20 and 1:10) the title compound (522 mg) was obtained.

δ ($^1$H, CDCl$_3$): 9.65 (s, 1H, CHO), 6.12 (dd, 1H, H2, J=1.2 and 3.3 Hz), 6.01 and 5.70 (2m, 2H, H$_2$C=), 5.91 and 5.77 (2d, 2H, OCH$_2$O, J=5.4 Hz), 4.91 (m, 2H, H2'+H1'), 4.74 (m, 1H, H3'), 4.37 (m, 2H, OCH$_2$C=), 4.03 (dd, 1H, H4', J=5.7 and 10.2 Hz), 3.91 (d, 1H, 8aCH$_2$(1H), J=8.7 Hz), 3.71–3.70 (m, 2H, 8aCH$_2$(1H)+H5'), 2.81 (t, 1H, H1, J=3.6 Hz), 2.25 (m, 1H, CH(CH$_3$)$_2$), 1.23 and 1.22 (2s, 9H, (CH$_3$)$_3$C).

INTERMEDIATE 10

[1R-(1α,3aβ,4β,4aβ,7β,7aα,8aβ)]8a-[(6-Deoxy-β-D-altropyranosyloxy)methyl]-4-formyl-4,4a ,5,6,7,7a,8,8a-octahydro-7-methyl-3-(1-methylethyl)-1,4methano-s-indacene-3a(1H)-carboxylic acid, diphenylmethyl ester To a solution of [1R-(1α,3aβ,4 ,4aβ,7β,7aα,8aβ)]8a-[(6-Deoxy-β-D-altropyranosyloxy)methyl]4-formyl4,4a,5,6,7, 7a,8,8a-octahydro-7-methyl-3-(1-methylethyl)-1,4-methano-s-indacene-3a(1H)-carboxylic acid, (10 g) in methanol (200 ml) was added dropwise at room temperature a 0.35M solution of .diphenyldiazomethane (90 ml) in methylene chloride, and the mixture was stirred for 6 hours. The solvent was evaporated to dryness and the residue chromatographed in a silica gel flash column with hexane-:ethyl acetate (3:1) as eluent to give the title compound (12.6 g) as a pale yellow foam.

δ ($^1$H, CDCl$_3$): 9.73 (s,1H, CHO), 6.98 (s,1H. C$\underline{H}$Ph$_2$), 6.05 (dd,1H, H-2, J=1.5 and 3.6 Hz), 4.65 (d, 1H, H-1', J=1.5 Hz), 4.09, 3.76 (2d, 2H, 8a-C$\underline{H}_2$, J=9Hz), 4.01 (m, 1H, H-2'), 3.84 (m, 1H, H-3'), 3.75 (m, 1H, H-5'), 3.69 (m, 1H, H-4'), 2.73 (t,1H, H-1, J=4.2 Hz).

INTERMEDIATE 11

[1R-(1α,3aβ,4β,4aβ,7β,7aα,8aβ)]8a-](6-Deoxy-3,4-O-isopropylidene-β-D-altropyranosyloxy)methyl]-4-formyl4, 4a,5,6,7,7a,8,8a-octahydro-7-methyl-3-(1-methylethyl)-(1H)-1,4-methano-s-indacene-3a(1H)-carboxylic acid, diphenylmethyl ester To a solution of Intermediate 10 (650 mg) in 15 ml of dimethoxypropane:acetone (1:2) was added p-toluensulphonic acid (10 mg). The solution was stirred at room temperature for 1.5 hours, then potassium carbonate (1.0 g) was added, the stirring continued for 30 minutes and the solvent evaporated to dryness. The crude mixture was partitioned between ethyl acetate (50 ml) and water (25 ml), the aqueous phase was extracted with ethyl acetate (2×50 ml), the organic phase was washed with brine, dried over magnesium sulphate and evaporated to dryness. The residue was flash chromatographed on silica gel eluting with ethyl acetate:hexane (1:3) to give the title compound (600 mg) as a white foam.

δ ($^1$H, CDCl$_3$): 9.73 (s, 1H, CHO), 7.45–7.24 (m, 10H, 2Ph), 6.98 (s, 1H, CHPh$_2$), 6.06 (dd, 1H, H-2, J=1.5 and 3.3 Hz), 4.57 (d, 1H, H-1', J=3.0 Hz), 4.30 (dd, 1H, H-3', J=3.6 and 5.7 Hz), 4.07 (d, 1H, 8aCH$_2$, J=9.0 Hz), 3.95–3.93 (m, 1H, H-2'), 3.85 (dd,1H, H4', J=5.7 and 9.3 Hz), 3.75 (d,1H, 8aCH2, J=9.0 Hz), 3.44 (dq, 1H, H-5', J$_d$=9.3 Hz, J$_q$=6.3 Hz), 2.73 (t,1H, H-1, J=3.6 Hz).

INTERMEDIATE 12

[1R-(1α,3aβ,4β,4aβ,7β,7aα,8aβ)]8a-[(2.6-Dideoxy-2-iodo-3.4-3,4-O-isoproiylidene-β-D-allopyranosyloxy)methyl]-4-formyl-4,4a,5,6,7,7a,8,8a-octahydro-7-methyl-3-(1-methylethyl)-1,4-methano-s-indacene-3a(1H)-carboxylic acid, diphenylmethyl ester.

A stirred solution of Intermediate 11 (2.055 g), triphenylphosphine (2.36 g) and imidazole (0.612 g) in dry toluene (40 ml) was heated at 100° C. and treated dropwise with a solution of iodine (1.53 g) in dry tetrahydrofuran (15 ml). The mixture was refluxed for 5 hours, cooled and partitioned between ethyl acetate (100 ml) and 1N aqueous hydrochloric acid (50 ml). The organic layer was washed successively with 1N aqueous hydrochloric acid, water, aqueous sodium metabisulfite solution, water and brine, then dried, filtered and concentrated in vacuo. The residue was flash chromatographed on silica gel eluting with hexane-:ethyl acetate (9:1) to obtain the title compound (1.2 g) as a white foam.

δ ($^1$H, CDCl$_3$): 9.70 (s, 1H, CHO), 7.5–7.2 (m, 10H, 2Ph), 6.95 (s, 1H, C$\underline{H}$Ph$_2$), 6.15 (dd, 1H, H-2, J=1.5 and 3.6 Hz), 4.50 (d, 1H, H-1', J=9 Hz), 4.41 (t, 1H, H-3', J=4.2 Hz), 4.05

(dd, 1H, H-2', J=3.9 and 9 Hz), 4.03 and 3.65 (2d, 2H, 8a-CH$_2$, J=9 Hz), 3.71 (dd, 1H, H-4', J=4.5 and 9.3 Hz), 3.53 (dq, 1H, H-5', J$_q$=6.6 Hz, J$_d$=9.3 Hz), 2.98 (t, 1H, H-1, J=3.6 Hz).

INTERMEDIATE 13

1R-(1α,3aβ,4β,4aβ,7β,7aα,8aβ)]8a-[(2,6-Dideoxy-2-iodo-β-D-allopyranosyloxy)methyl]-4-formyl4,4a ,5,6,7,7a,8,8a-octahydro-7-methyl-3-(1-methylethyl)-1,4-methano-s-indacene-3a(1H)-carboxylic acid, 2-(trimethylsilyl)ethyloxymethyl ester.

A solution of Intermediate 12 (620 mg) in dry dichloromethane (12 ml) was treated dropwise with 96% formic acid (4 ml) and stirred at room temperature for 8 hours. The reaction mixture was diluted with dichloromethane (50 ml) and water (50 ml) was added. The organic layer was washed with water (3×50 ml) and brine, then dried and evaporated to give a crude which was dissolyed in a mixture of tetrahydrofuran:methanol (v:v 2:1, 15 ml) and treated with 1N aqueous hydrochloric acid (5 ml). After stirring for 36 hours the mixture was partitioned between ethyl acetate (50 ml) and water (50 ml). The organic layer was washed with water (2×50 ml) and brine, dried and evaporated to dryness. The residue was dissolyed in dry tetrahydrofuran (10 ml) and treated at 0° C. with triethylamine (0.22 ml) and 2-(trimethylsilyl)ethyloxymethyl chloride (0.18 ml). The reaction mixture was stirred at 0° C. for 1.5 hours, methanol (0.3 ml) was added and stirring continued for 0.5 hours. Ethyl acetate (50 ml) and 1N aqueous hydrochloric acid (50 ml) were added and the two phases partitioned. The organic layer was washed with 1N aqueous hydrochloric acid, water and brine, then dried and evaporated. The residue was chromatographed (silica gel, hexane:ethyl acetate 3:1) to afford the title compound (500 mg) as a white foam.

δ ($^1$H, CDCl$_3$): 9.69 (s, 1H, CHO), 6.15 (dd, 1H, H-2, J=1.5 and 3.3 Hz), 5.4 and 5.25 (2d, 2H, OCH$_2$O, J=6 Hz), 4.53 (d, 1H, H-1', J=9 Hz), 4.20 (m, 1H, H-3'), 4.09 (dd, 1H, H-2', J=2.7 and 9 Hz), 3.93 and 3.63 (2d, 2H, 8a-CH$_2$, J=9 Hz), 3.80–3.66 (m, 3H, H-5' and Me$_3$SiCH$_2$CH$_2$O), 3.42 (m, 1H, H-4'), 2.98 (t, 1H, H-1, J=3.9 Hz), 0.03 (s, 9H, (CH$_3$)$_3$Si).

INTERMEDIATE 14

[1R-(1α,3aβ,4β,4aβ,7β,7aα,8aβ)]8a-[(2,3-Didehydro-2,3,6-trideoxy-β-D-allonyranosyloxy) methyl]-4-formyl4,4a,5,6,7,7a,8,8a-octahydro-7-methyl-3-(1-methylethyl)-1,4-methano-s-indacene-3a(1H)-carboxylic acid, 2-trimethylsilylethyioxymethylester.

A solution of Intermediate 13 (72 mg), triphenylphosphine (131 mg) and imidazole (34 mg) in dry tetrahydrofuran (5 ml) was stirred for 15 minutes and treated with iodine (64 mg) portionwise. After stirring at room temperature for 10 minutes, zinc powder (30 mg) was added and the reaction mixture stirred at 60° C. for 20 minutes. Purification by preparative TLC (silica gel, hexane:ethyl acetate 7:3) gave the title compound (35 mg).

δ ($^1$H, CDCl$_3$): 9.70 (s, 1H, CHO), 6.08 (dd, 1H, H-2, J=1.5 and 3.6 Hz), 5.96–5.70 (m, 2H, H-2' and H-3'), 5.45 and 5.26 (2d, 2H, OCH$_2$O, J=6 Hz), 4.95 (dd, 1H, H-1', J=1.8 and 3.3 Hz), 3.95–3.53 (m, 6H, 8a-CH$_2$, H-4', OCH$_2$—CH$_2$Si and H-5'), 2.79 (t, 1H, H-1, J=3.9 Hz), 0.03 (s, 9H, (CH$_3$)$_3$Si).

INTERMEDIATE 15

[1R-(1α,3aβ,4β,4aβ,7β,7aα,8aβ)]8a[(6-Deoxy-β-D-altropyranosyloxy)methyl]-4-formyl-4,4a,5,6,7,7a,8,8a-octahydro-7-methyl-3-(1-methylethyl)-1,4-methano-s-indacene-3a(1H)-carboxylic acid, pivaloyloxymethyl ester A mixture of [1R-(1α,3aβ,4β4aβ,7β,7aα,8aβ)]8a-[(6-Deoxy-β-D-altropyranosyloxy)methyl]4-formyl4,4a,5,6,7,7a,8,8a-octahydro-7-methyl-3-(1-methylethyl)-1,4-methano-s-indacene-3a(1H)-carboxylic acid, (10.00 g) and tetra n-butylammonium iodide (3.86 g) in N,N-dimethylformamide (70 ml) was stirred and treated with diisopropylethylamine (5.5 ml) and chloromethyl pivalate (3.3 ml). Then the resulting solution was heated at 50–55° under nitrogen. After 5.25 h the reaction mixture was treated with water (40 ml) and then after a further 0.25 h more water (240 ml) was added. After a further 1h the solid was collected by vacuum filtration, washed with water (3×20 ml) and then dried to give the title compound (11.71 g).

δ ($^1$H, DMSO.d$_6$): 0.77δ (3H) d, J=6.7 Hz; 0.87δ (3H), J=6.7 Hz; 0.94δ (1H) m; 0.98δ (3H) d, J=6.9 Hz; 1.14δ (3H) d, J=6.2 Hz; 1.16δ (1H) m; 1.19δ (9H) s; 1.55–2.05δ (9H) m; 2.17δ (1H) m; 2.77δ (1H) t, J=3.8 Hz; 3.29δ (1H) m; 3.49δ (1H) m; 3.55δ (1H) d, J=9.4 Hz; 3.67δ (1H) m; 3.70δ (1H) d, J=9.4 Hz; 4.44δ (3H) m; 4.78δ (1H) d, J=3.7 Hz; 5.81δ (1H) d, J=6.2 Hz; 5.91δ (1H) d, J=6.2 Hz; 6.13δ (1H) d, J=3.8 Hz; 9.60δ (1H) s.

INTERMEDIATE 16

[1R-(1α,3aβ,4β,4aβ,7β,7aα,8aβ)]8a-[(4-O-(2-Bromo-2-propenyl)-6-deoxy-β-D-altropyranosyloxy)methyl]-4-formyl-4,4a,5,6,7,7a,8,8a-octahydro-7-methyl-3-(1-methylethyl)1,4-methano-s-indacene-3a(1H)-carboxylic acid, pivaloyloxymethyl ester.

A suspension of Intermediate 15 (1.08 g), 4 Å molecular sieves (activated powder, 2 g) and dibutyltin oxide (0.54 g) in dry toluene (60 ml) was refluxed for 2 hours under nitrogen atmosphere in a flash fitted with a Dean-Stark condenser, and then allowed to cool to room temperature (approximately 15 ml of azeotropic mixture were removed). 2,3-Dibromopropene (280 μl) and tetrabutylammonium fluoride (1M solution in tetrahydrofuran, 1.2 ml) were added consecutively and the mixture heated at 50° C. for 24 hours. Evaporation of the solvent gave a residue which was flash chromatographed over silica gel eluting with dichloromethane:acetone (98:2) to give the title compound (520 mg) as a foam.

δ ($^1$H, CDCl$_3$): 9.69 (s, 1H, CHO), 6.07 (dd, 1H, H-2, J=1.6 and 3.6 Hz), 5.9 and 5.78 (2d, 2H, OCH$_2$O, J=5.4 Hz), 5.90 and 5.64 (2m, 2H, C=CH$_2$), 4.64 (d, 1H, H-1', J=1.5 Hz), 4.19 (m, 3H, H-3' and OCH$_2$—C=), 3.81 (AB system, 2H, 8a-CH$_2$, J=9.3 Hz), 3.86 (dd, 1H, H-2', J=1.5 and 3.9 Hz), 3.78 (dq, 1H, H-5', J=6.3 and 9.0 Hz), 3.41 (dd, 1H, H4', J=3.0 and 9.0 Hz), 2.74 (t, 1H, H-1, J=4.5 Hz), 2.25 (m, 1H, CH(CH$_3$)$_2$).

INTERMEDIATE 17

[1R-(1α,3aβ,4β,4aβ,7β,7aα,8aβ)]8a-[(4-O-(2-Bromo-2-propenyl)-6-deoxy-2,3-di-O-(ghenyloxy)thiocarbonyl-β-D-altropyranosyloxy)methyl]-4-formyl-4,4a,5,6,7,7a,8,8a-ctahydro-7-methyl-3-(1-methylethyl)-1,4-methano-s-indacene-3a(1H)-carboxylic acid, pivaloyloxymethyl ester.

To a solution of Intermediate 16 (0.26 g) in dry dichloromethane (7.5 ml) were added 4-dimethylaminopyridine (0.28 9 g) and phenylchlorothionoformate (0.22 ml) at 0° C. The mixture was stirred for 4 hours while the cooling bath reached room temperature. The reaction mixture was directly applied to a flash silica gel column and the title comDound was eluted with hexane:acetone (92:8) giving a white foam (0.25 g) by concentration of the appropriate fractions.

δ ($^1$H, CDCl$_3$): 9.70 (s, 1H, CHO), 7.47–7.10 (m, 10H, 2×C$_6$H$_5$), 6.08 (dd, 1H, H-2, J=1.5 and 3.6 Hz), 6.05 (dd, 1H, H-3', J=3.0 and 5.4 Hz), 5.95 and 5.65 (2m, 2H, C=C H$_2$), 5.92 and 5.79 (2d, 2H, OCH$_2$O, J=5.4 Hz), 5.86 (dd, 1H, H-2', J=1.8 and 5.4 Hz), 4.91 (d, 1H, H-1', J=2.1 Hz), 4.30 and 4.18 (AB system, 2H, OCH$_2$C═), 4.02 (m, 1H, H-5'), 3.94 and 3.69 (AB system, 2H, 8a-CH$_2$, J=9.3 Hz), 3.76 (dd, 1H, H4', J=2.7 and 7.2 Hz), 2.81 (t, 1H, H-1, J=3.9 Hz), 2.26 (m, 1H, CH(CH$_3$)$_2$).

INTERMEDIATE 18

[1R-(1α,3aβ,4β,4aβ,7β,7aα,8aβ)]8a-[[1S,7R,9R]-2,8-Dioxa-9-methyl-4-methylene-cis-bicyclo[3,4,0]non-7-ylxymethyl]-4-formyl-4,4a,5,6,7,7a,8,8a-octahydro-7-methyl-3-(1-methylethyl)-1,4-methano-s-indacene-3a(1H)-carboxylic acid, trimethylsilylethyioxuvmethyl ester.

A solution of Example 2 (77 mg), trcutyltinhydnde (44 μl) and azoisobutyronitrile (2,2 mg) in dry toluene (3 ml) was teated to reflux and kept under this condition for 30 minutes. Elimination of the solvent gave a crude product which was purified by flash chromatography, using as eluent hexane-:ethyl acetate v:v 10:1. to give the title compound (50 mg).

δ ($^1$H, CDCl$_3$): 9.71 (s, 1H, CHO), 6.06 (dd, 1H, H2, J=1.2 and 3.3 Hz), 5.43 and 5.26 (2d, 2H, OCH$_2$O, J=6.3 Hz), 5.07 and 5.01 (2m. 2H, H$_2$C═), 4.3–4.5 (m, 3H, 2H3'+H7'), 3.87 and 3.63 (2d, 2H, 8aCH$_2$, J=9.3 Hz), 3.79 (dd, 1H, H1', J=7.2 and 8.7 Hz), 3.7 (m, 2H, OCHhd 2CH$_2$Si), 3.26 (dq, 1H. H9', J=6.3 and 9.3 Hz), 3.01 (bs, 1H, H5'), 2.77 (t, 1H, H1, J=3.9 Hz), 297 (spd, 1H, CH(CH$_3$)$_2$, J=6.6 and 1.2 Hz).

EXAMPLE 1

[1R-(1α,3aβ,4β,4aβ,7β,7aα,8aβ)]8a[6-deoxy-β-D-mannopyranosyloxy)methyl]-4-formyl-4,4a,5,6,7,7a,8,8a-octahydro-7-methyl-3-(1-methylethyl)-1,4-methano-s-indacene-3a(1H) carboxylic acid, (Compound (IX: R═H)).

*Sordaria araneosa* (IMI369677) A-as grown on Potato Dextrose agar until mature growth occurred. Two 6 mm plugs of the agar containing the growth were transferred to a 250 ml Erlenmeyer flask containing 50ml of medium FS.

| Medium FS | g/L |
| --- | --- |
| Peptone (Oxoid L34) | 10 |
| Malt extract (Oxoid L39) | 21 |
| Glycerol (Glycerine CP) | 40 |
| Junion 110 (Honeywell & Stein) | 1 |
| Distilled water | |

The culture was incubated at 25C for 6 days on a rotary shaker operated at 250 rpm with a 50 mm diameter orbital motion. The broth was mixed 1:1 with 20% glycerol, dispensed in 1 ml aliquots and stored at −80C.

A 1 ml suspension prepared as described above was used to inoculate a 250 ml Erlenmeyer flask containing 50 ml of medium FS. The culture was incubated at 25C for 5 days on a rotary shaker operated at 250 rpm with a 50 mm diameter orbital motion. 3% (v/v) portions of the developed inoculum were used to inoculate further 250 ml Erlenmeyer flasks containing medium FS (50 ml) and incubated as described above for 4 days.

120 ml of the bulked shake flask developed inoculum was used to inoculate 2×7 L fermenters containing 5 L of medium BSM53A4. The fermentations were controlled to a temperature of 25C. The cultures were agitated at 400 rpm and aerated at 2 Lpm. After 3 days fermentation, 10 L of bulked culture was used to inoculate a 780 L fermenter containing 450 L of medium BSM53A4.

| Medium BSM53A4 Ingredient | Supplier | g/L |
| --- | --- | --- |
| NH4H2PO4 | Fisons(Ar) | 10 |
| Glucidex32D | Roquette | 60 |
| Arkasoy | British Arkady | 20 |
| Dried CSL | Roquette | 16 |
| Meritose$^A$ | Tunnel Refineries | 44 |
| PPG2000 | K & K Greef | 0.5 |

Demineralised H2O
Natural pH (in the range 4.0–4.5)
$^A$Meritose sterilised separately as a 70% solution and added to batch post-sterilisation.

The fermentation was controlled to a temperature of 25C. The broth was agitated at 350 rpm and aerated at 450 Lpm. PPG2000 antifoam was added on demand to control foaming. Whole broth extracts were assayed for the presence of Compound (IX; R═H) by reverse phase HPLC. The culture was harvested after 11 days when the extract of a broth sample indicated a Compound (1X; R═H) titre of 1.26 g/L.

Isolation

Fermentation broth produced as described above was adjusted to pH9 with sodium hydroxide and, after lhr at ambient temperature, was filtered through Dicalite on a rotary vacuum filter (1% Dicalite was added to the broth as filter aid). The filtrate was adjusted to pH 4–5 with conc. sulphuric acid and the solution applied to a column of XAD-16 resin (25 L). The resin bed was washed with 0.1% phosphoric acid (10 column volumes) followed by acetonitrile:water 1:9 (10 column volumes) before the product was eluted with acetonitrile:water 60:40 (2 column volumes). Flow rate throughout the process was between 1–2 column volumes per hr. The eluate was concentrated to leave an aqueous residue of 5 L and a water-insoluble oil/tar. The aqueous residue was discarded. The oily residue, containing the target compound, was disolved in acetone (3.75 L) and the solution filtered. A portion of this solution was evaporated to dryness, redisolyed in ethyl acetate and the solution decanted leaving a brown residue. The ethyl acetate solution (1.46 L) was passed down a bed of Whatman DE-52 ion-exchange cellulose (1.2 kg) prepared in water-saturated ethyl acetate. Compound (IX; R═H) was present in the column effluent whilst impurities were retained. The bed was given a displacement wash with ethyl acetate. Fractions containing Compound (IX; R═H) were combined to give a solution (1.64 L) containing Compound (IX; R═H) (202 g).

Isolation of Compound (IX; R═H) as a Free Acid

The ethyl acetate solution from the above was extracted with 5×1 L portions of phosphate buffer (0.2M Na$_2$HPO$_4$:0.2MKH$_2$PO$_4$ 1:0.6) and the extracts combined. The combined aqueous extracts (pH 6.68) were washed with ethyl acetate (2.5 L). The spent ethyl acetate solution was combined with the ethyl acetate wash for further processing (see below). The washed aqueous extract was adjusted to pH 4.1 with H$_3$PO$_4$ and extracted with ethyl acetate (1×½ volume followed by 1×⅓ volume). The combined ethyl acetate extracts were washed with water (1 L) then evaporated to dryness to yield Compound (IX; R═H), (82 g).

The spent ethyl acetate and wash from above were concentrated by evaporation to 1 L. The concentrate was extracted with 5×1 L portions of phosphate buffer (0.125M-Na$_2$HPO$_4$/0.075M-KH$_2$PO$_4$) and the extracts combined. The combined aqueous extract was adjusted to pH4 with H$_3$PO$_4$ and extracted with 2×⅓ volumes of ethyl acetate. The combined ethyl acetate extracts were washed with ⅓ volume of water then evaporated to dryness to yield further compound of formula (IX; R═H; 111 g).

A 500 MHz proton NMR spectrum of a solution in deutero-methanol includes peaks [δ values with multipicities, coupling constants (Hz) and integration values in parentheses] centred at about:

0.82(d,7,3H); 0.98(d,7,3H); 1.04(d,7,3H); 1.30(d,6,3H); 2.31 (m,1H); 2.81 (m,1H); 3.18(dq,9,6,1H); 3.37(dd,9,3,1H); 3.75(d,9,1H); 3.81 (d,3,1H); 3.93(d,9,1H); 4.28(s, 1H); 6.09(brd,3,1H); 9.75(s,1H)

(b) Compound (IX; R=H) Lithium Salt

Compound (IX; R=H) (98.6 g) prepared as described above (second preparation) was dissolyed in acetonitrile (1.35 L) and water (100 ml) added. To this solution was added triethylamine (25 ml), then a solution of lithium chloride (15 g) in water (50 ml) added dropwise over a period of 45 min with stirring. After standing overnight at ambient temperature the crystalline product was filtered off, washed with ice-cold acetonitrile:water 9:1 (200 ml) and acetonitrile:water 95:5 (200 ml), then dried in vacuo over phosphorus pentoxide to yield the title compound (72 g).

A 500 MHz proton NMR spectrum of a solution in deuterium oxide includes peaks [δ values with multipicities, coupling constants (Hz) and integration values in parentheses] centred at about:

0.78(d,7,3H); 0.99(d,7,3H); 1.10(d,13,1H); 2.13(m,1H); 2.25(m,1H); 2.65(m,1H); 3.55(m,1H); 3.89(ABq,2H); 3.96 (brd,3,1H); 4.44(brs,1H); 6.09(brd,3.5,1 H); 6.09(brd,3.5, 1H); 9.74(s,1H)

EXAMPLE 2

[1R-(1α,3aβ,4β,4aβ,7β,7aβ,8aβ)]8a[4-O-(2-Bromo-2-proizenyl)-2,3-didehydro-2,3,6-trideoxy-β-D-allopyranosyloxymethyl]-4-formyl4,4a,5,6,7,7a,8,8a-octahydro-7-methyl-3-(1-methylethyl)-1,4-methano-s-indacene-3a(1H) carboxylic acid, trimethylsilylethyloxymethyl ester.

Method A

To a solution of Intermediate 3 (259 mg) in dry methanol was added a catalytic amount of sodium methoxide and the solution stirred at room temperature. After two hours, the reaction was neutralized by adding Amberlite, filtered and concentrated to dryness. Purification of the crude by flash chromatography gave 182 mg of Intermediate 15.

The Intermediate 15 (91 mg) was dissolyed in dichloromethane (2 ml). To this solution were added consecutively 50% sodium hydroxide (2 ml), cetyltrimethylammonium bromide (6.2 mg) and 2,3-dibromo-1-propene (55 μl). The mixture was vigorously stirred until completion of the reaction. The two phases were separated and the organic layer was washed with brine (5 ml). Concentration to dryness gave a crude which was purified by flash chromatography (eluent hexane:ethyl acetate v:v 10:1) to afford (56% overall yield) the title compound (82 mg) as a transparent oil.

δ ($^1$H, CDCl$_3$): 9.69 (s, 1H, CHO), 6.08 (dd, 1H, H2, J=1.5 and 3.3 Hz), 6.01 and 5.78 (2dt, 2H, H2'+H3', J=10.5 and 1.5 Hz), 5.91 and 5.61 (2m, 2H, H$_2$C=), 5.45 and 5.26 (2d, 2H, OCH$_2$O, J=6.3 Hz), 4.96 (m, 1H, H1'), 4.22–4.11 (m, 2H, OCH$_2$C=), 3.91 (d, 1H, 8aCH$_2$(1H), J=9.3 Hz), 3.8–3.6 (m, 4H, 8aCH$_2$(1H)+OCH$_2$CH$_2$Si+H5'), 2.79 (t, 1H, J=4.2), 2.29 (m, 1H, CH(CH$_3$)$_2$).

Method B

Intermediate 14 (91 mg) was dissolyed in dichloromethane (2 ml). To this solution were added consecutively 50% sodium hydroxide (2 ml), cetyltrimethylammonium bromide (6.2 mg) and 2,3-dibromo-1-propene (55 μl). The mixture was vigorously stirred until completion of the reaction. The two phases were separated and the organic layer was washed with brine (5 ml). Concentration to dryness gave a crude which was purified by flash chromatography (eluent hexane:ethyl acetate v:v 10:1) to afford 82 mg (56% overall yield) of the title compound as a transparent oil.

δ ($^1$H, CDCl$_3$): 9.69 (s, 1H, CHO), 6.08 (dd, $_1$H, H2, J=1.5 and 3.3 Hz), 6.0 and 5.78 (2dt, 2H, H2'+H3', J=10.5 and 1.5 Hz), 5.91 and 5.61 (2m, 2H, H$_2$C=), 5.45 and 5.26 (2d, 2H, OCH$_2$O, J=6.3 Hz), 4.96 (m, 1H, H1'), 4.22–4.11 (m, 2H, OCH$_2$C=), 3.91 (d, 1H, 8aCH$_2$(1H), J=9.3 Hz), 3.8–3.6 (m, 4H, 8aCH$_2$(1H)+OCH$_2$CH$_2$Si+H5'), 2.79 (t, 1H, J=4.2), 2.29 (m, 1H, CH(CH$_3$)$_2$).

EXAMPLE 3

[1R-(1α,3aβ,4β,4aβ,7β,7aα,8aβ)]8a[4-O-(2-bromo-2-propenyl)-2,3-didehydro-2,3,6-trideoxy-β-D-allopyranosyloxy)methy]-4-formyl4,4a,5,6,7,7a,8,8a-octahydro-7-methyl-3-(1-methylethyl)-1,4-methano-s-indacene-3a(1H) carboxylic acid, pivaloyloxymethyl ester.

Method A

A vigorously stirred suspension of Intermediate 5 (1 g), triphenylphosphine (1.47 g), triodoimidazole (1 g) and imidazole (190 mg) in dry toluene (40 ml) was heated to reflux for 6 h under nitrogen atmosphere. Water (10 ml) and solid sodium metabisulfite (800 mg) were added and the two phases stirred for 10 min. The organic layer was washed with 10% aqueous sodium metabisulfite (2×40 ml) and brine (2×40 ml), concentrated to dryness and purified by flash chromatography (Silica gel, Hexanes/ethyl acetate v/v 25:1, 20:1 and 15:1) to afford the title compound 620 mg as a transparent oil.

δ ($^1$H, CDCl$_3$): 9.69 (s,1H,CHO); 6.08 (dd, 1H, H2, J=1.2 and 4.5 Hz); 6.0)m, 1H, H2'); 5.9 (m, 2H, OCH$_2$O+CH$_2$=); 5.8 (m,2H,H3'+OCH$_2$O); 5.6 (m, 1H, CH$_2$=), 4.95 (m, 1H, H1'); 4.16 (m, 2H, CH$_2$O); 3.83 (d, 1H, 8aCH$_2$(1H), J=9.3 Hz); 3.8–3.6 (m, 3H, 8aCH$_2$(1H)+H4'+H5'); 2.78 (t, 1H, H1, J=3.9 Hz); 2.26 (m, 1H, CH(CH$_3$)$_2$); 1.23 (s, 9H, 3CH$_3$).

Method B

A solution of Intermediate 9 (150 mg) in trimethylphosphite (5 ml) was heated to reflux and kept under these conditions for 12 hours. Water (10 ml) and ethyl acetate (10 ml) were added and the mixture separated. The organic phase was concentrated to dryness to give a crude product which was purified by flash chromatography (hexane:ethyl acetate 7:1) to yield the title compound (4.6 mg, 34% yield) as a transparent oil.

EXAMPLE 4

[1R-(1α,3aβ,4β,4aβ, 7β,7aα,8aβ)]8a-[[1S,7R,9R]-2,8-Dioxa-9-methyl-4-methylene-cis-bicyclo[3,4,0]-non-7-yloxymethyl]4-formyl-4,4a,5,6,7,7a,8,8a-octahydro-7-methyl-3-(1-methylethyl)-1,4-methano-s-indacene-3a(1H)-carboxylic acid.

Method A

A solution of Intermediate 6 (80 mg) in dry methanol (1 ml) was treated with sodium methoxide (11 mg) and stirred at room temperature for 1 hour. The reaction mixture was partitioned between diethyl ether (50 ml) and 0.5 N aqueous hydrochloric acid (100 ml). The organic layer was washed with water (3×50 ml) and brine, then dried and evaporated to afford the title comDound (60 mg) as a white foam.

δ ($^1$H, CDCl$_3$): 9.87 (s, 1H, CHO), 6.04 (dd, 1H, H2, J=1.2 and 3.3 Hz), 5.08 and 5.02 (2m, 2H, CH$_2$=), 4.50–4.29 (m, 4H, H7'+2H3'+8aCH$_2$(1H)), 3.76 (dd, 1H, H1', J=9.3 and 7.5 Hz), 3.32–3.22 (m, 2H, 8aCH$_2$(1H)+H9'), 3.02 (bs, 1H, H5'), 2.45 (t, 1H, H1, J=3.6 Hz).

Method B

To a solution of Intermediate 18 in dry THF (1 ml) was added tetrabutylammonium fluoride (81 μl, 1M solution in tetrahydrofuran) and 4 A molecular sieves. The mixture was stirred at room temperature overnight. The solvent was removed to dryness, the residue dissolyed in dichloromethane (1 ml) and placed at the top of a silica column. Elution with acetone:hexane v:v 1:10 gave (96% yield) of the title compound 38 mg as an oil.

What is claimed is:

1. A process for the preparation of the compound (I)

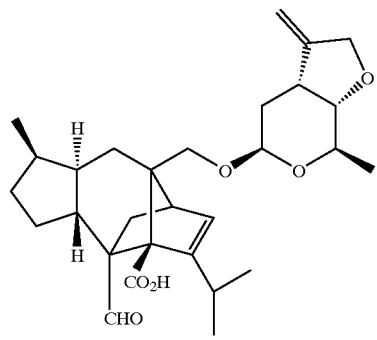

and pharmaceutically acceptable salts or metabolically labile esters thereof which comprises cyclisation of a compound of formula II

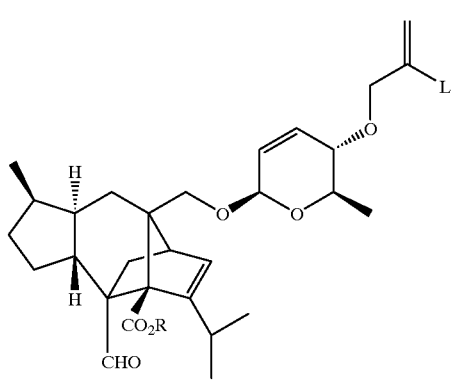

wherein L is a group capable of homolytic cleavage and R is hydrogen or a carboxyl protecting group, followed where necessary or desired by one or more of the following steps;

(I) removal of the carboxyl protecting group R;
(ii) isolation of the compound of formula (I) in the form of a physiologically acceptable salt thereof;
(iii) conversion of the resultant compound of formula (I) into a metabolically labile ester thereof.

2. A process as claimed in claim 1 wherein R is a carboxyl protecting group.

3. A process as claimed in claim 1 wherein the cyclisation is carried out using a radical chain carrier in the presence of a radical initiator.

4. A process as claimed in claim 1 wherein L is a bromine atom.

5. A compound of formula (II)

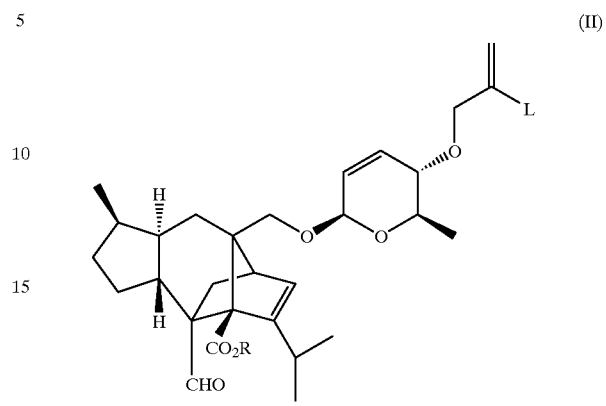

wherein R is hydrogen or a carboxy protecting group and L is a group capable of homolytic cleavage.

6. A compound as claimed in claim 5 wherein L is bromine.

7. A compound as claimed in claim 5 wherein R is a pivaloyloxymethyl or trimethylsilylethyloxymethyl group.

8. A compound of formula (IX)

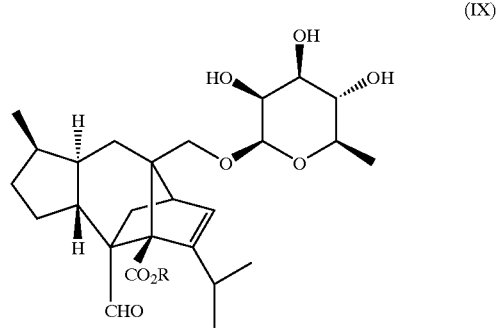

where R is hydrogen or a salt or a carboxy protected derivative thereof.

9. The lithium salt of the compound of formula (IX) wherein R is hydrogen.

10. A process for the preparation of a compound of formula (IX) wherein R is hydrogen or a salt thereof which comprises, cultivating a microorganism capable of producing the compound of formula (IX) and thereafter isolating the compound of formula (IX) wherein R is hydrogen or a salt thereof from the culture in substantially pure form.

* * * * *